United States Patent [19]

Maul et al.

[11] 4,440,696

[45] * Apr. 3, 1984

[54] PROCESS FOR PRODUCING TRIARYLPHOSPHITES

[75] Inventors: Rudolf Maul, Lorsch/Hessen; Eberhard Otto, Lindenfels; Horst Zinke, Ernsthofen, all of Fed. Rep. of Germany

[73] Assignee: Ciba-Geigy Corporation, Ardsley, N.Y.

[*] Notice: The portion of the term of this patent subsequent to Jan. 26, 1999 has been disclaimed.

[21] Appl. No.: 307,474

[22] Filed: Oct. 1, 1981

Related U.S. Application Data

[63] Continuation of Ser. No. 103,132, Dec. 13, 1979, Pat. No. 4,312,818, which is a continuation of Ser. No. 928,644, Jul. 27, 1978, abandoned.

[51] Int. Cl.$^3$ .............................................. C07F 9/141
[52] U.S. Cl. ..................................... 260/976; 260/967
[58] Field of Search .......................................... 260/976

[56] References Cited

U.S. PATENT DOCUMENTS

| | | | |
|---|---|---|---|
| 2,733,226 | 1/1956 | Hunter | 260/29.7 |
| 3,689,602 | 9/1972 | Ismail | 260/936 |
| 3,751,529 | 8/1973 | Baker et al. | 260/973 |
| 3,772,414 | 11/1973 | Baker et al. | 260/973 |
| 3,773,866 | 11/1973 | Baker et al. | 260/973 |
| 4,069,279 | 1/1978 | Boyden | 260/975 |
| 4,237,075 | 12/1980 | Gough | 260/976 |
| 4,312,818 | 1/1982 | Maul et al. | 260/976 |

FOREIGN PATENT DOCUMENTS 1168819 10/1969 United Kingdom .
448821 8/1975 U.S.S.R. .

*Primary Examiner*—Anton H. Sutto
*Attorney, Agent, or Firm*—Luther A. R. Hall

[57] ABSTRACT

A process for producing triarylphosphites of the formula $(RO)_3P$, in which R represents aryl or aryl substituted by one or more straight-chain or branched-chain alkyl, cycloalkyl, aryl or aralkyl groups, by reaction of phosphorous trihalides with hydroxy-substituted aromatic compounds of the formula ROH in the presence of 0.005 to 10 mol %, relative to the hydroxy-substituted aromatic compound, of a catalyst, optionally in the presence of a solvent, in which process the catalyst used is a compound from the group comprising amines or ammonium salts, amides of carboxylic and thiocarboxylic acids and also of oxygen acids of phosphorus, non-aromatic nitrogen-containing heterocycles and salts thereof, guanidines, amidines and azomethines and also salts thereof, sulfones, sulfoxides and sulfonium salts, primary, secondary and tertiary phosphines and salts thereof, phosphine oxides, phosphine sulfides or esters of phosphoric acids.

6 Claims, No Drawings

PROCESS FOR PRODUCING TRIARYLPHOSPHITES

This is a continuation of application Ser. No. 103,132, filed on Dec. 13, 1979, now U.S. Pat. No. 4,312,818, issued on Jan. 26, 1982, which in turn is a continuation of application Ser. No. 928,644, filed on July 27, 1978, now abandoned.

The present invention relates to a process for producing triarylphosphites from phosphorus trihalides and hydroxy-substituted aromatic compounds with the use of specific phosphorus-, nitrogen- and/or sulfur-containing compounds as catalysts.

It is known that triarylphosphites have become widely applied as stabilisers or co-stabilisers in the processing of, in particular, thermoplastics. The aryl groups therein can be substituted or unsubstituted. These triarylphosphites are generally produced by reacting phosphorus trihalides with hydroxy-substituted aromatic compounds. High temperatures have to be used for this reaction in order to obtain the highest possible conversion, especially where the aryl groups are substituted and the reactivity of the hydroxyl groups is impaired. Frequently however the high temperatures and relatively long reaction times are not sufficient to achieve a complete reaction, and a mixture consisting essentially of mono- and diaryloxyphosphorus halides and triaryl phosphites is obtained.

It has therefore already been suggested that this reaction be performed in the present of catalysts. Possible catalysts mentioned are alkali metal halides and alkaline-earth metal halides, such as LiCl, $MgCl_2$ or $CaCl_2$, metals such as Mg or Zn, and Lewis acids such as $ZnCl_2$ or $AlCl_3$; and organic compounds mentioned are nitrogen-containing aromatic heterocycles such as pyridine (see Russian Patent No. 488 821). These solutions are still not satisfactory and still require heating times which are too long at temperatures which are too high.

The quaternary phosphonium bases suggested in the Russian Patent No. 488 821 as being suitable catalysts are indeed distinguished by an increased reactivity, but are not sufficiently specific. With use in particular of substituted hydroxy-substituted aryls are obtained only mixtures consisting largely of diarylchloro- and triarylphosphites.

The aim of the present invention is to provide a process for producing triarylphosphites from phosphorus trihalides and hydroxy-substituted aromatic compounds, which renders possible, by the use of catalysts acting more reactively and more selectively, the obtainment of high yields at lower temperatures and with shortened reaction times, especially with the use of substituted hydroxy-substituted aromatic compounds.

The subject matter of the present invention is a process for producing triarylphosphites of the formula $(RO)_3P$, in which R represents aryl or aryl substituted by one or more straight-chain or branched-chain alkyl, cycloalkyl, aryl or aralkyl groups, by reaction of phosphorus trihalides with hydroxy-substituted aromatic compounds of the formula ROH in the presence of 0.005 to 10 mol %, relative to the hydroxy-substituted aromatic compound, of a catalyst, optionally in the presence of an inert solvent, in which process the catalyst used is a compound from the group comprising amines or ammonium salts, amides of carboxylic and thiocarboxylic acids and of oxygen acids of phosphorus, non-aromatic nitrogen-containing heterocycles and salts thereof, guanidines, amidines and azomethines and salts thereof, sulfones, sulfoxides and sulfonium salts, primary, secondary and tertiary phosphines and salts thereof, phosphine oxides, phosphine sulfides or esters of phosphoric acids.

Where R represents aryl in the formula $(RO)_3P$, it is for example naphthyl and especially phenyl, which can be substituted as defined. The substituents can be in any position on the aryl, and preferably no more than three substituents are present.

In the case of the phenyl groups, the substituents are preferably in the 2-, 4- and/or 6-positions. The 2,4-position is particularly preferred. If substituents are in the 2,6-positions, they should not be large space-filling substituents, for example tertiary alkyl groups. According to the process of the invention, there are then obtained reaction mixtures in which are present mainly undesired chlorophosphites. It is therefore in the case of the process according to the invention out of the question for two substituents having a tertiary α-C atom to be in the 2,6-positions; if there is therefore bound in the 2-position a group having a tertiary α-C atom, there is bound in the 6-position a secondary C atom, preferably however a primary C atom.

The aryl can be substituted by straight-chain or branched-chain alkyl. This preferably contains 1 to 18, especially 1 to 12 C atoms. Examples which may be mentioned are: methyl, ethyl, n-propyl, iso-propyl, n-butyl, i-butyl, t-butyl, pentyl, hexyl, heptyl, n-octyl, t-octyl, n-nonyl, i-nonyl, decyl, n-dodecyl, tetra-decyl, hexadecyl, octadecyl and eicosyl. The alkyl can also be substituted or interrupted by cycloalkyl, for example cyclohexylmethyl or methylcyclohexylethyl. The aryl can also be substituted by cycloalkyl preferably having 5 to 6 ring carbon atoms, which can also be substituted by alkyl. Examples are: cyclopentyl, cyclohexyl, methylcyclohexyl, ethylcyclohexyl, octylcyclohexyl and cyclooctyl. The aryl can also be substituted by aryl, preferably phenyl and aralkyl, preferably benzyl or α- or β-phenylethyl. The aryl group can here be substituted by alkyl groups preferably having 1 to 8 C atoms. Examples are methylphenyl, ethylphenyl and methylbenzyl.

Some examples of hydroxy-substituted aromatic compounds of the formula ROH are phenol, α- or β-naphthol, methylnaphthol, 2- or 4-methylphenol, 2- or 4-ethylphenol, 2- or 4-propyl- as well as -isopropylphenol, 2- or 4-n-butyl-, i-butyl- and also t-butylphenol, pentyl-, hexyl-, heptyl-, n-octyl-, tert-octyl-, nonyl-, decyl-, dodecyl-, octadecylphenol, cyclohexyl-, phenyl- or benzylphenol, 2,4- or 2,6-dimethyl-, diethyl-, dipropyl-, diisopropyl-, di-n-butyl-, di-i-butylphenol, 2,4-di-tert-butylphenol, 2-methyl-4-ethylphenol, 2-methyl-4-tert-butylphenol, 2-tert-butyl-4-methylphenol, 2-methyl-4-n-octylphenol, 2,4,6-trimethylphenol, 2,4,6-triisopropylphenol, 2,6-dimethyl-4-octylphenol and 2-methyl-4-benzylphenol.

Among the phosphorus halides, which are used as starting compounds for carrying out the process according to the invention, phosphorus trichloride is particularly preferred. There are preferably used stoichiometrical amounts of the reactants in order to avoid additional purifying operations. It can occasionally be of advantage if a slight excess, for example up to 10%, of the hydroxy-substituted aromatic compound is used. The catalyst is preferably used in amounts of 0.05 to 5 mol %, especially 0.1 to 2 mol %.

The process according to the invention can be performed at temperatures of 10° C. to preferably 150° C., particularly between 20° and 130° C. Higher temperature are generally not necessary, a factor which is to be considered as being especially advantageous.

The process according to the invention can be performed without solvent. The concomitant use of a solvent however has proved to be advantageous. Suitable solvents are for example: ethers such as diethyl ether, tetrahydrofuran and dioxane, aliphatic and aromatic hydrocarbons such as hexane, heptane, petroleum ether, cyclohexane, methylcyclohexane, benzene, toluene and xylene, chlorinated hydrocarbons such as methylene chloride, chloroform, dichloroethane and carbon tetrachloride.

The process is performed according to the invention in the presence of selected catalysts. The N atoms of the amines and ammonium salts, of the amides and nitrogen-containing heterocycles, of the guanidines, amidines and azomethines and of salts thereof, or the sulfones, sulfoxides, sulfonium compounds, phosphines, phosphine oxides and phosphine sulfides, can carry alkyl, cycloalkyl, aryl, here particularly phenyl, alkaryl, here especially alkylated phenyl, aralkyl, here particularly benzyl or alkaralkyl, here especially alkylated benzyl, which are optionally interrupted by oxygen or sulfur atoms, and which preferably contain 1 to 18, in particular 1 to 12 C atoms. The alkyl contains especially 1 to 6 C atoms, and cycloalkyl is in particular cyclopentyl and cyclohexyl.

The catalysts to be used according to the invention in the form of salts are preferably halides, particularly chlorides. The salts can also be formed in situ by means of the hydrogen halide being formed during the process. It is nevertheless in some cases advantageous to use the salts themselves as catalysts. One group of catalysts comprises the amines and ammonium salts. The amines can be primary, secondary and tertiary amines and also salts thereof. The salts include also the quaternary ammonium salts. The secondary amines and salts thereof and the quaternary ammonium salts are preferred. Likewise preferred are the alkyl- and cycloalkyl-substituted amines, such as the cyclic amines, which are classed with the non-aromatic heterocycles. Examples are: methyl-, ethyl-, propyl-, n-butyl-, t-butyl-, pentyl-, octyl-, dodecyl-, phenyl-, benzyl-, dimethyl-, diethyl-, methylethyl-, methylbutyl-, methyloctyl-, methylphenyl-, ethylbenzyl-, trimethyl-, triethyl-, tributyl-, octyldimethyl- and dimethylphenylamine, and also tetramethyl-, trimethylethyl-, triethylmethyl-, tributylmethyl-, tetrabutyl-, trimethyloctyl-, triphenylmethyl- and tribenzylmethylammonium chloride, -bromide or -iodide. Examples of further ammonium salts are methyl-, octyl-, dimethyl-, methylcyclohexyl-, dibenzyl-, diphenyl-, trimethyl-, tributyl-, tribenzyl- and triphenylammonium chloride, -bromide and -iodide. The amines and ammonium salts can also contain aromatic N-heterocyclic radicals, for example pyridyl. These amines are more effective than the pure aromatic N-heterocycles.

A further group of catalysts comprise the amides of carboxylic and thiocarboxylic acids and also of oxygen acids of phosphorus. This group includes also the ureas, thioureas and bisurea derivatives thereof. The amides can be derived from polyfunctional, preferably monofunctional, carboxylic acids or thiocarboxylic acids, which contain in particular 1 to 14 C atoms. The acids can also be derived from aromatic N-heterocycles. It has been found that these amides are considerably more effective than the aromatic N-heterocycles from which they are derived. Also suitable are cyclic amides, for example ε-caprolactam. The amides derived from carboxylic acids and thiocarboxylic acids correspond preferably to the formula

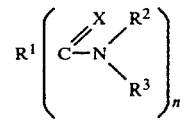

in which, where n is 1, $R^1$ is phenyl, benzyl, naphthyl, cyclohexyl, cyclopentyl, pyridyl, hydrogen or alkyl having 1 to 13 C atoms, preferably 1 to 6 C atoms; where n is 2, $R^1$ is phenylene, naphthylene, cyclohexylene or alkylene having 1 to 12 C atoms, preferably 1 to 6 C atoms, or a direct bond; X is an oxygen or sulfur atom; and $R^2$ and $R^3$ independently of one another are each a hydrogen atom, phenyl, benzyl, cyclohexyl and alkyl having 1 to 12 C atoms, preferably 1 to 6 C atoms, or $R^2$ and $R^3$ together are alkylene which is optionally interrupted by O or S atoms and which preferably has 4-7 C atoms. Examples are formamide, oxalic acid diamide, dimethylformamide, acetamide, thioacetamide, N,N-dimethylacetamide or -thioacetamide, picolineanilide, thiopicolineanilide, benzoic acid amide, terephthalic acid diamide and trimellitic acid triamide.

The oxygen acids of phosphorus, from which the amides can be derived, are for example phosphoric acid, phosphorous acid, hypophosphorous acid, phosphonic acid or phosphinic acid. Phosphoric acid and phosphonic acids are preferred. Examples of such amides are phosphoric acid triamide, hexamethylphosphoric acid triamide, methylphosphonic acid diamide, phenylphosphonic acid-N,N-tetramethyldiamide and N,N'-(dimethyl)phenylphosphonic acid diamide.

Examples of the amides of carbonic acid or thionocarbonic acid which may be mentioned, in addition to urea and thiourea, are: tetramethylurea or -thiourea, diphenyl- or dibenzylurea or -thiourea, diethylurea, di-n-octylurea or -thiourea and also bisurea derivatives, for example ethylenebisurea and N,N-tetramethylphenylenethiourea. Examples of cyclic ureas are hydantoin and benzimidazolone.

A further group of catalysts suitable for the process according to the invention are non-aromatic N-heterocycles. These can contain more than one N atom and also O and S atoms. They can also be unsaturated. They can be in the form of salts, and also in the form of quaternary ammonium bases and the N atoms can be substituted, preferably by alkyl groups having 1 to 12 C atoms. Examples are: pyrrolidine, $\Delta^3$-pyrroline, N-methylpyrrolidine, dihydroindole, pyrazolidine, imidazolidine, $\Delta^2$-pyrazoline, 1-phenylpyrazolidine, oxazolidine, thiazolidine, oxazoline, triazolidine, oxadiazolidine, thiadiazolidine, piperidine, morpholine, N-methylmorpholine, quinolidine, 1,2-dihydropurine and 8-aza-bicyclo-(3,2,1)-octane.

To be mentioned under the guanidines, besides guanidine itself, are n-alkylated, benzylated and phenylated derivatives, for example tetramethyl- or tetrabutylguanidine and N,N'-bisphenylguanidine. Suitable salts are principally the halides.

A further group of catalysts comprises the azomethines and amidines and salts thereof, preferably the halides. They can be represented by the following formula:

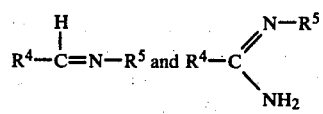

in which $R^4$ is phenyl, benzyl, cyclohexyl, a hydrogen atom or alkyl having 1 to 8 C atoms, preferably 1 to 4 C atoms, and $R^5$ is a hydrogen atom or phenyl, benzyl, cyclohexyl or alkyl having 1 to 18 C atoms, preferably 1 to 8 C atoms. Examples which may be mentioned are: acetamidine hydrochloride N-methylacetamidine, benzylideneanilide and N-butylpropionamidine.

The sulfones and sulfoxides used as catalysts can be straight-chain or cyclic and they can contain further functional groups, for example ester groups. Examples are: dimethylsulfone, dimethylsulfoxide, tetra- or pentamethylenesulfone, tetramethylenesulfoxide and bis-carboisooctyloxydimethylsulfoxide.

Preferred among the sulfonium salts are the sulfonium iodides, for example trimethylsulfonium iodide, dimethylethylsulfonium iodide and triethylsulfonium iodide. Also the salts, particularly the iodides, of the sulfoxides are suitable, for example trimethylsulfoxonium iodide.

A further group of catalysts to be used according to the invention are the primary, secondary and tertiary phosphines and salts, oxides and sulfides thereof. Those preferred are the tertiary phosphines, the salts, oxides and sulfides thereof, and preferred among the salts are the hydrohalides, especially the chlorides, bromides and iodides. The phosphorus atom can carry phenyl, benzyl, cyclohexyl and alkyl having 1 to 12 C atoms, preferably 1 to 6 C atoms. Examples are: methylphosphine, ethylphosphine, hexylphosphine, dodecylphosphine, dimethyl-, ethylmethyl-, diphenyl-, dicyclohexyl-, dibenzyl-, phenylmethylphosphine, triphenyl-, tribenzyl, tricyclohexyl-, trimethyl-, triethyl-, tripropyl-, tributyl-, triisobutyl-, tripentyl-, trihexyl- and dimethylphenylphosphine, and their hydrochlorides, -bromides and -iodides as well as -oxides and -sulfides.

The esters of phosphoric acid are derived preferably from phosphonic acids and phosphoric acids. The alcohol radicals of the esters are derived preferably from phenols and especially from $C_1$-$C_{18}$ alkanols and also from cycloalkanols, for example phenol, 2-methylphenol, cyclohexanol, methanol, ethanol, propanol, butanol, hexanol, octanol, i-octanol, dodecanol and octadecanol. Examples of phosphonic acids are: phenyl-, benzyl-, cyclohexyl-, methyl-, ethyl-, propyl-, butyl-, pentyl- and hexylphosphonic acid.

The process according to the invention is performed in devices known to be suitable for the purpose. In general, the hydroxy-substituted aromatic compound is placed, optionally together with a solvent, into the reaction vessel; the phosphorus trihalide is then added and, after addition of the catalyst, the reaction mixture is stirred until the reaction is complete. Stirring is preferably carried out with heating in order to accelerate the reaction.

It is however also possible to place the hydroxy-substituted aromatic compound, optionally a solvent, and the catalyst into the reaction vessel, and to then slowly add the phosphorus trihalide. It has proved advantageous in some cases to slightly warm the prepared mixture, for example up to 60° C., preferably up to 40° C.

After all the phosphorus halide has been added, stirring is continued to complete the reaction, optionally with heating up to 150° C.

The hydrogen halide formed is with advantage continuously removed during the reaction, and a vacuum can be used to effect complete separation. The isolation of the desired triarylphosphites is performed, using known methods, by distillation or crystallisation, optionally after removal of the solvent.

With the process according to the invention are obtained, surprisingly under mild conditions, triarylphosphites within relatively short reaction times, with a high degree of purity and in excellent yields. A particularly advantageous feature of this process is that this also applies to production using substituted hydroxy-substituted aromatic compounds as reactants, particularly those in which the reactivity of the hydroxyl groups is impaired by steric hinderance.

The triarylphosphites produced according to the invention are suitable as stabilisers or co-stabilisers, together with for example phenolic antioxidants, for the processing of thermoplastic polymers, for example polyolefins.

The examples which follow illustrate the invention in greater detail.

EXAMPLE 1

61.91 g (0.3 mol) of 2,4-di-tert.-butylphenol in 135 ml of toluene is placed into a 250 ml three-necked round flask provided with thermometer, magnetic stirrer and attached gas-discharge tube; 13.73 g (0.1 mol) of phosphorus trichloride is then added and, after the addition of 0.003 mol of the respective catalyst, the reaction mixture is stirred at 22°-26° C. for 7 hours. The liberated hydrogen chloride is passed through the gas-discharge tube and through a small attached bubble counter into an absorption receiver and absorbed with about 300 ml of water. The acid content of the absorption receiver is subsequently determined by titration with 0.1 N sodium hydroxide solution.

The test results summarised in the following Table 1 illustrate the surprisingly high degree of effectiveness of the catalyst systems.

| Test No. | Catalyst | Conc.* (Mol %) | Absorbed amount of HCl (g of HCl/7 hrs) |
|---|---|---|---|
| 0 | — | — | 0.0002 |
| 1 | tribenzylamine | 1.0 | 0.21 |
| 2 | diisopropylamine | 1.0 | 2.74 |
| 3 | dicyclohexylamine | 1.0 | 2.88 |
| 4 | morpholine | 1.0 | 2.38 |
| 5 | benzylamine | 1.0 | 0.27 |
| 6 | dimethylformamide | 1.0 | 1.38 |
| 7 | N,N—dimethylacetamide | 1.0 | 1.32 |
| 8 | thioacetamide | 1.0 | 4.86 |
| 9 | benzylideneaniline | 1.0 | 2.30 |
| 10 | tetramethylammonium chloride | 1.0 | 3.40 |
| 11 | 1,5-diazabicyclo[5'4'0]-undec-5-ene | 1.0 | 2.92 |
| 12 | tetramethylguanidine | 1.0 | 2.78 |
| 13 | N—formylmorpholine | 1.0 | 2.50 |
| 14 | 2-methyl-$\Delta^2$-oxazoline | 1.0 | 3.43 |
| 15 | p-dimethylaminopyridine | 1.0 | 2.78 |
| 16 | α-thiopicolineanilide | 1.0 | 2.56 |
| 17 | methanephosphonic acid dimethyl ester | 1.0 | 0.63 |
| 18 | 2-aminothiazole | 1.0 | 2.74 |
| 19 | dimethylsulfoxide | 1.0 | 1.04 |
| 20 | triisobutylphosphine | 1.0 | 1.73 |

| Test No. | Catalyst | Conc.* (Mol %) | Absorbed amount of HCl (g of HCl/7 hrs) |
|---|---|---|---|
| | oxide | | |
| 21 | bis-carbon-isooctyl-oxymethylsulfoxide | 1.0 | 1.68 |
| 22 | tetramethylenesulfoxide | 1.0 | 1.83 |
| 23 | trimethylsulfoxonium-iodide | 1.0 | 0.11 |
| 24 | tributylphosphine | 1.0 | 3.10 |
| 25 | triphenylphosphine | 1.0 | 2.69 |

*relative to the employed amount of 2,4-di-tert.-butylphenol

EXAMPLE 2

The reaction with phosphorus trichloride and 2,4-di-tert.-butylphenol is performed according to Example 1. Chloroform is used as solvent in place of toluene.

The results of the tests are summarised in the following Table 2.

TABLE 2

| Test No. | Catalyst | Conc. (Mol %) | Absorbed amount of HCl (g of HCl/7 hrs) |
|---|---|---|---|
| 1 | — | | 0.00012 |
| 2 | tetramethylthiourea | 1.0 | 4.08 |
| 3 | acetamidine hydrochloride | 1.0 | 3.06 |
| 4 | trimethylsulfonium-iodide | 1.08 | 4.47 |
| 5 | thioacetamide | 1.0 | 5.45 |

EXAMPLE 3 (COMPARATIVE EXAMPLE)

For purposes of comparison, 2,4-ditert.-butylphenol is reacted with phosphorus trichloride according to Example 1, with various known products being used as catalysts. The results are summarised in Table 3.

TABLE 3

| Test No. | Catalyst | Conc. (mol %) | Absorbed amount of HCl (g of HCl/7 hrs) |
|---|---|---|---|
| 1 | — | — | 0.0002 |
| 2 | lithium chloride | 10 | 0.0128 |
| 3 | calcium chloride | 10 | 0.0648 |
| 4 | aluminum chloride | 1 | 0.009 |
| 5 | magnesium | 1 | 0.0137 |
| 6 | magnesium oxide | 1 | 0.005 |
| 7 | zinc | 1 | 0.0694 |
| 8 | zinc chloride | 10 | 0.046 |
| 9 | pyridine | 1.0 | 0.6 |
| 10 | α-picoline | 1.0 | 0.7 |

The results of the comparison tests show that only a small increase in the reaction rate in the reaction of phosphorus trichloride with sterically hindered phenols can be obtained by using the catalysts known hitherto.

EXAMPLE 4

247.6 g of 2,4-di-tert.-butylphenol (1.2 mols), 39 g of xylene and 0.8 g of dimethylformamide (0.011 mol) are placed into a 500 ml round flask and heated to 40° C. In the course of 15 minutes, 54.9 g of phosphorus trichloride (0.4 mol) is added dropwise; the mixture is stirred for 1 further hour at 40°-50° C., then heated to 130° C. and stirred for 1 hour at this temperature. In order to remove the hydrogen chloride still contained in the reaction mixture, stirring is carried out for 1 hour at 120°-130° C. under reduced pressure (about 200 mm Hg), with a part of the solvent being removed at the same time.

To isolate the product, the reaction mixture is diluted with isopropanol. The tris-(2,4-di-tert.-butylphenyl)-phosphite which has crystallised out is filtered off, washed with isopropanol and dried to give 221 g of product (85.4% yield) having a melting point of 186°-187° C. The phosphite is very pure and contains only traces of 2,4-di-tert.-butylphenol.

We claim:

1. A process for producing a triaryl phosphite of the formula (RO)₃P, in which R represents aryl substituted by one or more straight-chain or branched-chain alkyl, cycloalkyl, aryl or aralkyl groups in the 2-, 2,4-, 2,6- or 2,4,6-positions, by reaction of a phosphorus trihalide with a hydroxy-substituted aromatic compound of the formula ROH in the presence or absence of a solvent, and in the presence of 0.005 to 10 mol %, relative to the hydroxy-substituted aromatic compound, of a catalyst selected from the group consisting of (a) an amide of a carboxylic acid of the formula

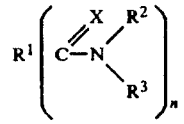

in which, where n is 1, R¹ is phenyl, benzyl, naphthyl, cyclohexyl, cyclopentyl, pyridyl or alkyl having 1 to 13 C atoms; where n is 2, R¹ is phenylene, naphthylene, cyclohexylene or alkylene having 1 to 12 C atoms, or a direct bond; X is an oxygen atom; and R² and R³ independently of one another are each a hydrogen atom, phenyl, benzyl, cyclohexyl or alkyl having 1 to 12 C atoms, or R² and R³ together are alkylene which is optionally interrupted by O or S atoms;

(b) a primary, secondary or tertiary amine in which alkyl, cycloalkyl, aryl, alkaryl, aralkyl or alkaralkyl of 1 to 18 C atoms is linked to the N atom; and (c) a saturated or unsaturated non-aromatic N-heterocyclic compound which is pyrrolidine, Δ³-pyrroline, N-methylpyrrolidine, dihydroindole, pyrazolidine, imidazolidine, Δ²-pyrazoline, 1-phenylpyrazolidine, oxazolidine, thiazolidine, oxazoline, triazolidine, oxadiazolidine, thiadiazolidine, piperidine, morpholine, N-methylmorpholine, quinolidine, 1,2-dihydropurine, 8-aza-bicyclo-[3.2.1]-octane, 1,5-diazabicyclo[5.4.0]-undec-5-ene, 2-methyl-Δ²-oxazoline or 2-aminothiazole.

2. A process according to claim 1 wherein the hydroxy-substituted aromatic compound ROH is 2-methyl-, ethyl-, n-propyl-, isopropyl-, n-butyl-, isobutyl-, tert-butyl-, pentyl-, hexyl-, heptyl-, n-octyl-, tert-octyl-, nonyl-, decyl-, dodecyl-, octadecylphenol, cyclohexyl-, phenyl- or benzylphenol, 2,4- or 2,6-dimethyl-, diethyl-, dipropyl-, diisopropyl-, di-n-butyl-, di-i-butylphenol, 2,4-di-tert-butylphenol, 2-methyl-4-ethylphenol, 2-methyl-4-tert-butylphenol, 2-tert-butyl-4-methylphenol, 2-methyl-4-n-octylphenol, 2,4,6-trimethylphenol, 2,4,6-triisopropylphenol, 2,6-dimethyl-4-octylphenol or 2-methyl-4-benzylphenol.

3. A process according to claim 1 wherein the amide catalyst is oxaldiamide, acetamide, N,N-dimethylacetamide, picolineanilide, benzamide, terephthaldiamide or trimellitictriamide.

4. A process according to claim 1 wherein the amine catalyst is methyl-, ethyl-, propyl-, n-butyl-, t-butyl-, pentyl-, octyl-, dodecyl-, phenyl-, benzyl-, dimethyl-, diethyl-, methylethyl-, methylbutyl-, methyloctyl-, methylphenyl-, ethylbenzyl-, trimethyl-, triethyl-, tributyl-, octyldimethyl-, dimethylphenyl-, tribenzyl-, diisopropyl- or dicyclohexylamine.

5. A process according to claim 4 wherein the amine catalyst is dicyclohexylamine.

6. A process according to claim 1 wherein the catalyst is morpholine.